(12) United States Patent
Anderson et al.

(10) Patent No.: US 11,076,884 B2
(45) Date of Patent: Aug. 3, 2021

(54) INTRODUCER WITH EXPANDABLE CAPABILITIES

(71) Applicant: BOSTON SCIENTIFIC SCIMED, INC., Maple Grove, MN (US)

(72) Inventors: James M. Anderson, Corcoran, MN (US); Adam David Grovender, Maple Grove, MN (US); Brian R. Reynolds, Ramsey, MN (US); Ross A. Olson, Anoka, MN (US); Heather Hetteen, Robbinsdale, MN (US); Uchenna Junior Agu, Baton Rouge, LA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 177 days.

(21) Appl. No.: 15/874,056

(22) Filed: Jan. 18, 2018

(65) Prior Publication Data
US 2018/0199960 A1 Jul. 19, 2018

Related U.S. Application Data

(60) Provisional application No. 62/447,543, filed on Jan. 18, 2017.

(51) Int. Cl.
*A61B 17/34* (2006.01)
*A61B 17/02* (2006.01)
(Continued)

(52) U.S. Cl.
CPC ...... *A61B 17/3423* (2013.01); *A61B 17/0218* (2013.01); *A61F 2/2427* (2013.01);
(Continued)

(58) Field of Classification Search
CPC ............ A61B 17/0218; A61B 17/3423; A61B 17/3417; A61B 17/3439; A61B 1/32;
(Continued)

(56) References Cited

U.S. PATENT DOCUMENTS

| 5,320,611 A | 6/1994 | Bonutti et al. |
| 7,837,692 B2 | 11/2010 | Mulholland et al. |

(Continued)

FOREIGN PATENT DOCUMENTS

| EP | 2995268 A1 | 3/2016 |
| WO | 2016164082 A1 | 10/2016 |

OTHER PUBLICATIONS

Invitation to Pay Additional Fees dated Jul. 2, 2018 for International Application No. PCT/US2018/014147.

*Primary Examiner* — Kathleen S Holwerda
*Assistant Examiner* — Brooke Labranche
(74) *Attorney, Agent, or Firm* — Seager, Tufte & Wickhem LLP

(57) ABSTRACT

An example introducer is disclosed. An example introducer sheath includes a tubular member including an inner surface, an outer surface and a wall extending therebetween. The introducer further includes a plurality of spine members. The plurality of spine members are positioned radially inward of the outer surface of the tubular member. Further, each of the plurality of the spine members are positioned radially outward of the inner surface of the tubular member. Additionally, the tubular member is designed to shift from a first configuration to a second configuration and the wall has a first thickness in the first position and a second thickness in the second position, the second thickness smaller than the first thickness.

10 Claims, 10 Drawing Sheets

(51) Int. Cl.
*A61M 39/02* (2006.01)
*A61F 2/24* (2006.01)
*A61M 25/00* (2006.01)
*A61M 25/06* (2006.01)

(52) U.S. Cl.
CPC ...... *A61M 25/005* (2013.01); *A61M 25/0662* (2013.01); *A61M 39/0247* (2013.01); *A61M 2039/0258* (2013.01); *A61M 2039/0279* (2013.01)

(58) Field of Classification Search
CPC ....... A61B 1/303; A61B 1/31; A61B 17/3421; A61F 2/2427; A61M 2039/0258; A61M 2039/0279; A61M 25/005; A61M 25/0662; A61M 39/0247
See application file for complete search history.

(56) References Cited

U.S. PATENT DOCUMENTS

| | | | |
|---|---|---|---|
| 2008/0004571 A1 | 1/2008 | Voss | |
| 2010/0198160 A1 | 8/2010 | Voss | |
| 2016/0095622 A1* | 4/2016 | Clancy | A61B 1/307 600/204 |
| 2016/0296332 A1 | 10/2016 | Zhou et al. | |

* cited by examiner

INTRODUCER WITH EXPANDABLE CAPABILITIES

CROSS-REFERENCE TO RELATED APPLICATIONS

This application claims the benefit of priority under 35 U.S.C. § 119 to U.S. Provisional Application Ser. No. 62/447,543, filed Jan. 18, 2017, the entirety of which is incorporated herein by reference.

TECHNICAL FIELD

The disclosure relates generally to medical devices and more particularly to medical devices that are adapted for use in percutaneous medical procedures.

BACKGROUND

In some instances, performing percutaneous medical procedures may require the insertion and/or maneuvering of relatively large medical devices through a patient's vasculature. However, inserting the medical device into the vasculature may result in undesirable forces being applied to the vessel walls. For example, as the medical device passes into the vasculature, it may make undesirable contact with one or more vessel walls. This interference may cause injury to the vessel as the medical device is navigated into calcified or diseased vessels. Therefore, in some instances an introducer is utilize to facilitate the insertion of medical devices into the vessel. Further, vessel trauma resulting from forces applied to the vessel wall by a medical device may be lessened by minimizing the size of an introducer used to access the vessel. Therefore, it may be desirable to design an introducer having a reduced insertion profile, yet capable of expansion when necessary (e.g., during the passage of a medical device therethrough).

SUMMARY

This disclosure provides design, material, manufacturing method, and use alternatives for medical devices. An example introducer sheath includes a tubular member including an inner surface, an outer surface and a wall extending therebetween. The introducer further includes a plurality of spine members. The plurality of spine members are positioned radially inward of the outer surface of the tubular member. Further, each of the plurality of the spine members are positioned radially outward of the inner surface of the tubular member. Additionally, the tubular member is designed to shift from a first configuration to a second configuration and the wall has a first thickness in the first position and a second thickness in the second position, the second thickness smaller than the first thickness.

Alternatively or additionally to any of the examples above, wherein each of the plurality of spine members are embedded within the wall of the tubular member.

Alternatively or additionally to any of the examples above, wherein each of the plurality of spine members are circumferentially spaced away from one another around the longitudinal axis of the tubular member.

Alternatively or additionally to any of the examples above, wherein the tubular member includes a proximal region and a distal region, and wherein each of the plurality of spine members extends from the proximal region to the distal region.

Alternatively or additionally to any of the examples above, wherein each of the plurality of spine members extends helically around the longitudinal axis of the tubular member.

Alternatively or additionally to any of the examples above, wherein the wall has a third thickness in the second position, and wherein the third thickness is smaller than the second thickness.

Alternatively or additionally to any of the examples above, wherein the wall tapers from the third thickness to the second thickness.

Alternatively or additionally to any of the examples above, wherein each of the plurality of spine members are spaced away from one another and wherein the third thickness is located between each of the adjacent spine members.

Alternatively or additionally to any of the examples above, wherein each of the plurality of spine members are positioned within the second wall thickness.

Alternatively or additionally to any of the examples above, wherein the tubular member includes a first outer diameter in the first position and a second outer diameter in the second position, and wherein the second outer diameter is larger than the first outer diameter.

Alternatively or additionally to any of the examples above, wherein the tubular member includes a third outer diameter in the second position and wherein the third outer diameter is smaller than the second outer diameter.

Alternatively or additionally to any of the examples above, wherein the tubular member includes a first inner radius in the first position and a second inner radius in the second position, the second inner radius larger than the first inner radius.

Alternatively or additionally to any of the examples above, wherein the tubular member includes a third inner radius in the second position, and wherein the third inner radius is larger than the second inner radius.

Another example introducer includes:

a hub;

a transition member having a proximal portion, a distal portion and a constant outer diameter from the distal portion to the proximal portion; and an expandable member having a proximal portion and a distal portion, the proximal portion of the expandable member coupled to the distal portion of the transition member;

wherein the proximal portion of the transition member is coupled to a distal portion of the hub;

wherein the expandable member further includes a plurality of spine members spaced around a longitudinal axis of the expandable member;

wherein the expandable member is designed to shift from an unexpanded configuration to an expanded configuration.

Alternatively or additionally to any of the examples above, wherein the expandable member includes a first wall thickness in the unexpanded configuration and a second wall thickness in the expanded configuration, the second wall thickness smaller than the first wall thickness.

Alternatively or additionally to any of the examples above, wherein each of the plurality of spine members are embedded within the wall of the expandable member.

Alternatively or additionally to any of the examples above, each of the plurality of spine members are positioned along an inner surface of expandable member.

A method of treating the heart includes:
  positioning an introducer assembly within a body lumen, the introducer assembly including:
    a hub;
    a transition member having a proximal portion, a distal portion and a constant outer diameter from the distal portion to the proximal portion; and
    an expandable member having a proximal portion and a distal portion, the proximal portion of the expandable member coupled to the distal portion of the transition member;
    wherein the proximal portion of the transition member is coupled to a distal portion of the hub member;
    wherein the expandable member further includes a plurality of spine members spaced around a longitudinal axis of the expandable member; and
  advancing a heart valve through the introducer assembly, whereby the expandable member expands from an unexpanded configuration to an expanded configuration to accommodate the heart valve.

Alternatively or additionally to any of the examples above, wherein each of the plurality of spine members are embedded within the wall of the expandable member.

Alternatively or additionally to any of the examples above, wherein each of the plurality of spine members are positioned along an inner surface of expandable member.

The above summary of some examples is not intended to describe each disclosed embodiment or every implementation of the present disclosure. The Figures, and Detailed Description, which follow, more particularly exemplify these examples.

Figure 1:
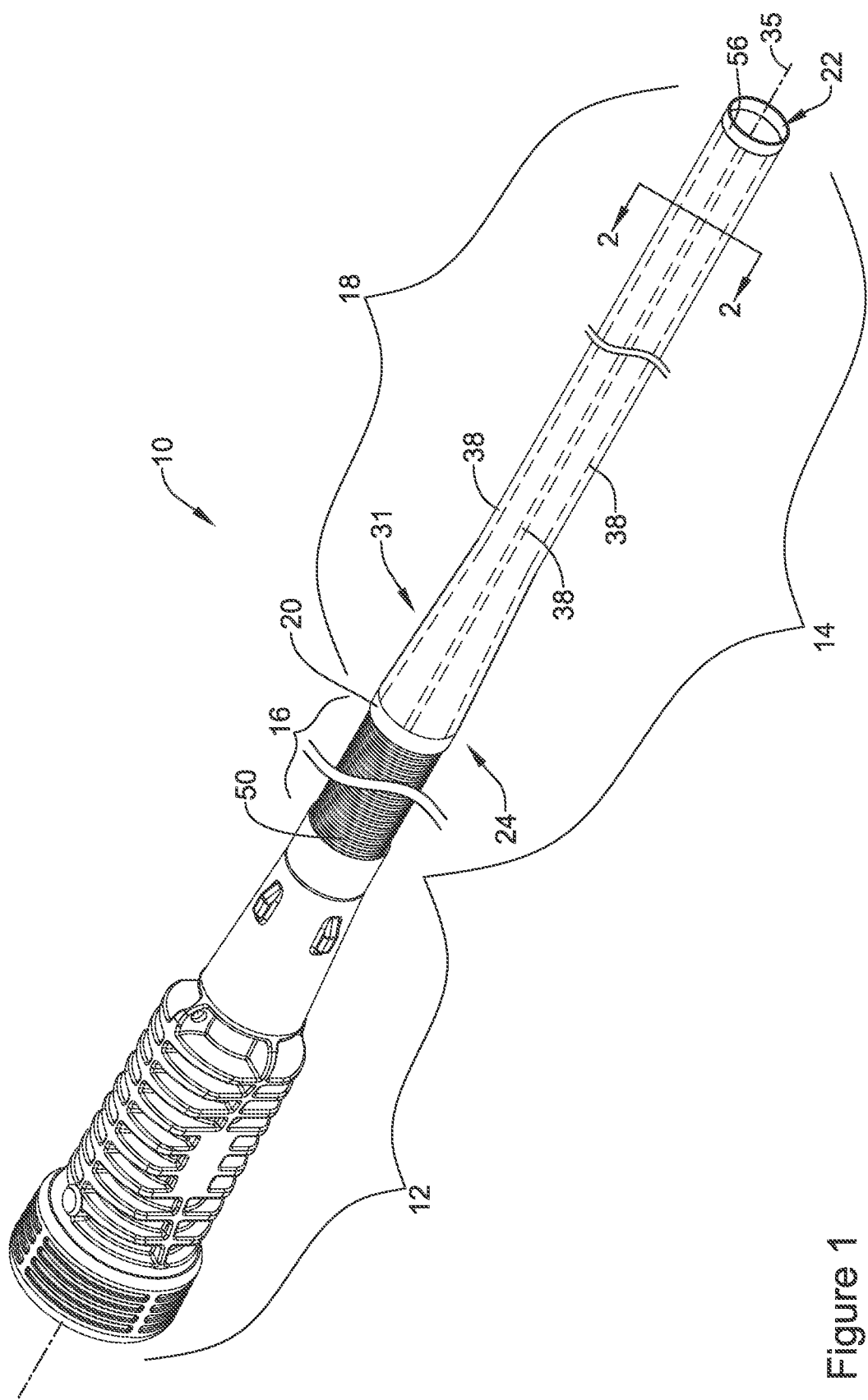
FIG. 1 is a perspective view of an example introducer.

While the disclosure is amenable to various modifications and alternative forms, specifics thereof have been shown by way of example in the drawings and will be described in detail. It should be understood, however, that the intention is not to limit the disclosure to the particular examples described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some examples", "other examples", etc., indicate that the embodiment described may include one or more particular features, structures, and/or characteristics. However, such recitations do not necessarily mean that all examples include the particular features, structures, and/or characteristics. Additionally, when particular features, structures, and/or characteristics are described in connection with one embodiment, it should be understood that such features, structures, and/or characteristics may also be used connection with other examples whether or not explicitly described unless clearly stated to the contrary.

The following detailed description should be read with reference to the drawings in which similar elements in different drawings are numbered the same. The drawings, which are not necessarily to scale, depict illustrative examples and are not intended to limit the scope of the disclosure.

In some instances, performing percutaneous medical procedures may require the insertion and/or maneuvering of relatively large medical devices through a patient's vasculature. However, inserting the medical device into the vasculature may result in undesirable forces being applied to the vessel walls. For example, as the medical device passes into the vasculature, it may make undesirable contact with one or more vessel walls. This interference may cause injury to the vessel as the medical device is navigated into calcified or diseased vessels. Therefore, in some instances an introducer is utilize to facilitate the insertion of medical devices into the vessel. Further, vessel trauma resulting from forces applied to the vessel wall by a medical device may be lessened by minimizing the size of an introducer used to access the vessel. Therefore, it may be desirable to design an introducer having a reduced insertion profile, yet capable of expansion when necessary (e.g., during the passage of a medical device therethrough). The following examples disclose an intravascular medical device including an expandable introducer, whereby the introducer is designed to expand from a reduced profile, unexpanded configuration to an expanded configuration.

FIG. 1 illustrates an example expandable introducer (e.g., delivery sheath, access sheath, etc.) 10. The introducer 10 may include a tubular member 14 attached to a hub member 12. The tubular member 14 may include a proximal section 16 and a distal section 18. The tubular member 14 may further include a lumen 22 extending therethrough.

Introducer 10 may include a tapered region 31. In some examples, the tapered region 31 may be positioned distal to the proximal section 16 of introducer 10. In some examples at least a portion of distal portion 18 of introducer 10 may have a substantially constant outer diameter which transitions into tapered portion 31. At least a portion of tapered portion 31 may have an outer diameter which is greater than the outer diameter of at least a portion of distal section 18. However, this is not intended to be limiting. It is contemplated that any portion of the introducer 10 may include any number of tapers, constant diameter regions or combinations thereof.

The proximal section 16 of the tubular member 14 may include a spring member 50. In some examples, an outer covering or sheath may cover either the outer surface, inner surface or both the inner and outer surfaces of the spring member 50. For example, in some instances, the spring member 50 may be positioned between (e.g., laminated) a covering positioned along the outer surface of spring member 50 and a covering positioned along the inner surface of the spring member 50.

Additionally, the hub 12 may include a hemostatic valve or seal disposed therein. The hemostatic valve or seal may prevent blood or other bodily fluid(s) from flowing proximally through the lumen 22 of the tubular member 14. In at least some examples, the hub 12 may include a port in fluid communication with the lumen 22 of the tubular member 14.

FIG. 1 further illustrates that introducer 10 may include one or more reinforcement members 38 extending along the distal section 18. The proximal ends 24 of the reinforcement members 38 may be attached to a collar 20. It can further be appreciated from FIG. 1 that the collar 20 may be attached to the proximal section 16 of the tubular member 14. It is further contemplated that in at least some examples, the proximal ends 24 of the reinforcement members 38 may be connected directly to the distal end of the proximal section 16. Further, in some examples the collar 20 or the reinforcement members 38 may be directly coupled to the spring member 50.

In some examples it may be desirable to add a tip member to the distal end of any of the examples disclosed herein. FIG. 1 shows an example tip member 56 disposed along the distal section 18. Tip member 56 may be designed with a low durometer material. In some instances, a lower durometer material may provide tip member 56 with the ability to radially expand (e.g., flex) outward and radially contract as a variety of medical devices are advanced through tip member 56. Further, tip member 56 may include a taper. For example, tip member 56 may taper from a first diameter to a second diameter at the distal end of introducer 10. While not intended to be limiting, in some examples the shape of tip member 56 may resemble a bull-nose. Additionally, tip member 56 may include a radiopaque material. The radiopaque material may allow tip member 56 to be visualized by a clinician during a medical procedure. In some examples, the tip may be segmented radially and/or dissected such that it may separate into segments upon expansion.

Figure 2:
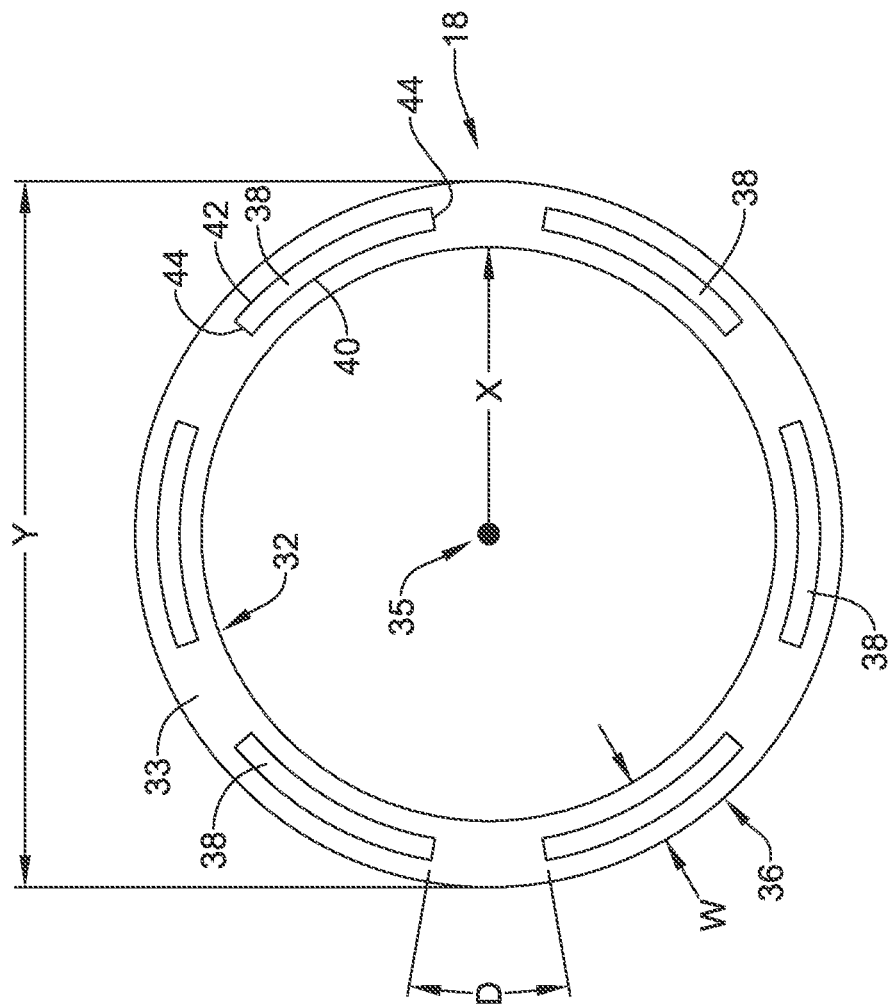
FIG. 2 is a cross-sectional view of an example introducer taken along the line 2-2 of FIG. 1.

FIG. 2 shows a cross-sectional view along line 2-2 of FIG. 1. FIG. 2 illustrates a cross-section taken along the distal section 18 of the tubular member 14. As will be described in greater detail below, FIG. 2 represents a cross-section of tubular member 14 in an unexpanded configuration.

As shown in FIG. 2, the distal section 18 of the tubular member 14 may include an outer diameter depicted as "Y." Further, the distal section 18 of the tubular member 14 may include an inner radial extent (measured from the central longitudinal axis 35 of the distal section 18 to the inner surface 32 of the distal section 18) depicted as "X." Additionally, FIG. 2 shows that distal section 18 of the tubular member 14 may include a wall thickness "W" defined as width of the tubular wall between the inner surface 32 and outer surface 36 of the distal section 18 of tubular member 14.

FIG. 2 further illustrates the plurality of reinforcement members 38 positioned within the wall 33 of the distal section 18 of the tubular member 14. For example, FIG. 2 shows six reinforcement members 38 positioned circumferentially around the longitudinal axis 35 of the distal section 18 of the tubular member 14. However, while FIG. 2 shows six reinforcement members 38 positioned around the longitudinal axis 35 of the distal section 18 of the tubular member 14, it is contemplated that more greater or less than six reinforcement members 38 may be utilized for any example introducers 10 contemplated herein. For example, tubular member 14 may include 1, 2, 3, 4, 5, 6, 7, 8, 9, 10, 15 or more reinforcement members 38 positioned along tubular member 14. In some examples, the reinforcement members 38 may include one or more materials (e.g., nylon, Vestamid®, polyimide, polyester, metals, etc.) which are stiffer, higher durometer materials than the material for which the distal section 18 of the tubular member 14 is constructed.

Further, FIG. 2 shows that in some examples, the width of reinforcement members 38 may be substantially uniform. In other words, the width of reinforcement members 38 may remain substantially uniform along the length distal section 18. However, it is contemplated that the width of one or more of the reinforcement members 38 may taper along the distal section 18 of the tubular member 14 (e.g., taper toward the tip member 56).

Each of the reinforcement members 38 shown in FIG. 2 may include an inwardly-facing surface 40, an outwardly-facing surface 42 and two end surfaces 44. Further, FIG. 2 shows that the inner surface 40 of each of the reinforcement members 38 may be positioned radially outward of the inner surface 32 of the distal section 18 of the tubular member 14. Further, the outer surface 42 of each of the reinforcement members 38 may be positioned radially inward of the outer surface 36 of the distal section 18 of the tubular member 14. In other words, each of the reinforcement members 38 may be embedded (e.g., encased, surrounded, etc.) within the wall thickness "W" of the distal section 18 of the tubular member 14.

Additionally, FIG. 2 illustrates that each of the reinforcement members 38 may be circumferentially spaced apart from one another around the longitudinal axis 35 of the distal section 18 of the tubular member 14. For example, FIG. 2 shows the ends 44 of each of the reinforcement members 38 may be spaced apart from one another a distance depicted as "D" in FIG. 2. In some instances, the reinforcement members 38 may be spaced substantially equidistant from one another. In other words, the spacing "D" may be substantially equivalent between individual adjacent reinforcement members 38. However, it is further contemplated that reinforcement members 38 may be spaced at variable distances around the longitudinal axis 35. Additionally, it can be appreciated that the distance "D" depicted in FIG. 2 may vary along the wall thickness of distal section 18. For example, the distance "D" may increase as it is measured from an end 44 of a reinforcement member 38 to an adjacent end 44 of an adjacent reinforcement member 38.

As discussed above, in some examples it may be desirable to design introducer 10 to permit a medical device (e.g., heart valve) to pass therethrough. For example, it may be desirable to permit a medical device to pass through hub 12, proximal section 16 and distal section 18 (for example, to pass through introducer 10 while being inserted into a body lumen). Further, in some instances it may be desirable to design introducer 10 to radially expand such that it can accommodate devices which have an outer diameter greater than the unexpanded inner diameters of hub 12, proximal section 16 and distal section 18.

Figure 3:
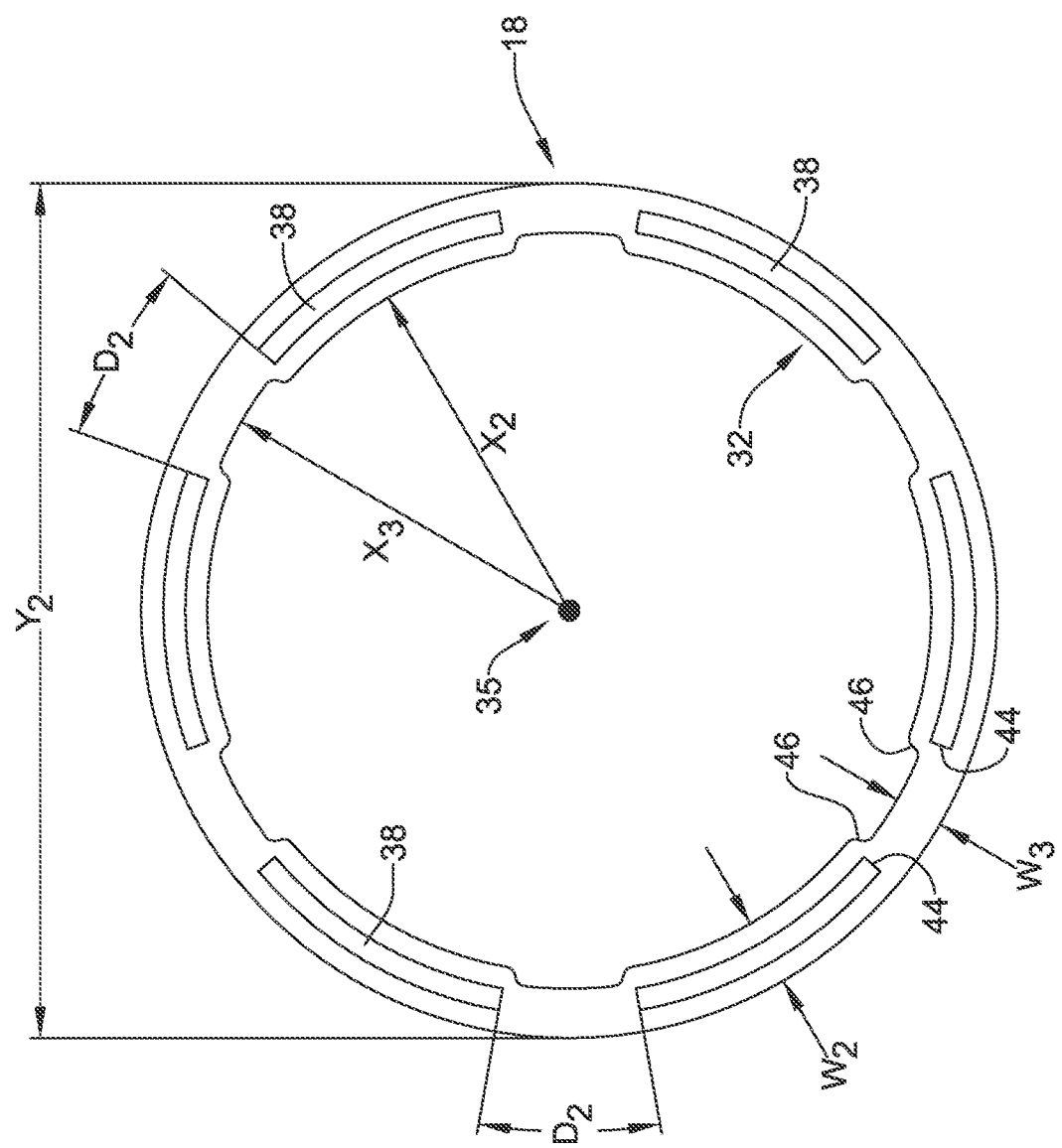
FIG. 3 is a cross-sectional view of an example introducer in an expanded configuration.

FIG. 3 represents the distal section 18 of tubular member 14 in an expanded configuration. For example, FIG. 3 may represent the cross-section of the tubular member 14 shown in FIG. 2 after it has been expanded radially outward. Stated another way, the distal section 18 of the tubular member 14 may shift from a first position to a second position. In some examples, the first configuration may represent an unexpanded configuration while the second configuration may represent an expanded configuration.

As shown in FIG. 3, the distal section 18 of the tubular member 14 may include an outer diameter depicted as "$Y_2$." It can be appreciated that the expanded outer diameter $Y_2$ may be greater than the unexpanded diameter Y shown in FIG. 2. Further, the distal section 18 of the tubular member 14 may include an expanded inner radial extent (measured from the central longitudinal axis 35 of the distal section 18 to the inner surface 32 of the distal section 18) depicted as "$X_2$." It can be appreciated that the expanded inner radius $X_2$ may be greater than the unexpanded inner radius X shown in FIG. 2.

It can be appreciated that as an example introducer 10 is expanded from an unexpanded configuration to an expanded configuration (as shown in FIG. 2 and FIG. 3, respectively), the wall thickness of the distal section 18 and/or the thickness of the reinforcement members 38 may decrease. In other words, as the distal section 18 of tubular member 14 expands, the material defining the distal section 18 and/or one or more of the reinforcement members 38 may stretch as the distal section 18 of the tubular member 14 expands radially outward. This stretching of the distal section 18 of the tubular member 14 may cause the wall thickness of the distal section 18 to decrease.

Additionally, FIG. 3 shows the wall thickness of the expanded distal section 18 depicted as "$W_2$." Wall thickness $W_2$ represents the wall thickness of the expanded distal section 18 of tubular member 14. Further, FIG. 3 shows wall thickness $W_2$ taken along the portion of the cross-section of the distal section 18 which includes the reinforcement members 38. In other words, wall thickness $W_2$ represents the wall thickness of the portion of the tubular wall of distal section 18 that includes one of the reinforcement members 38.

In some examples, the expanded distal section 18 of tubular member 14 may include a third wall thickness. For example, FIG. 3 illustrates a wall thickness depicted as "$W_3$" taken along the portion of the cross-section of the distal section 18 which does not include the reinforcement members 38. For example, FIG. 3 shows the space between each of the reinforcement members 38 as "$D_2$." It can be appreciated that as the distal section 18 of tubular member 14 expands, the space between adjacent reinforcement members 38 may increase. In other words, the space $D_2$ may be greater than D (depicted in FIG. 2).

Further, FIG. 3 illustrates that wall thickness $W_3$ may be less than wall thickness $W_2$. For example, it is contemplated that the portion of the wall of the distal section 18 of the tubular member 14 may taper down (e.g., neck down) around the ends 44 of the reinforcement members 38. FIG. 3 shows that the wall thickness of the distal section 18 of the tubular member 14 may include tapered sections 46. The tapered sections 46 may be defined as a transition region from wall thickness $W_2$ to wall thickness $W_3$.

It can be appreciated that in examples that include a wall thickness $W_3$, the distal section 18 of tubular member 14 may include a second expanded inner radial extent (measured from the central longitudinal axis 35 of the distal section 18 to the inner surface 32 positioned along distance $D_2$ described above) depicted as "$X_3$." It can be appreciated that the second expanded inner radius $X_3$ may be greater than the expanded inner radius $X_2$ illustrated in FIG. 3.

Figure 4:
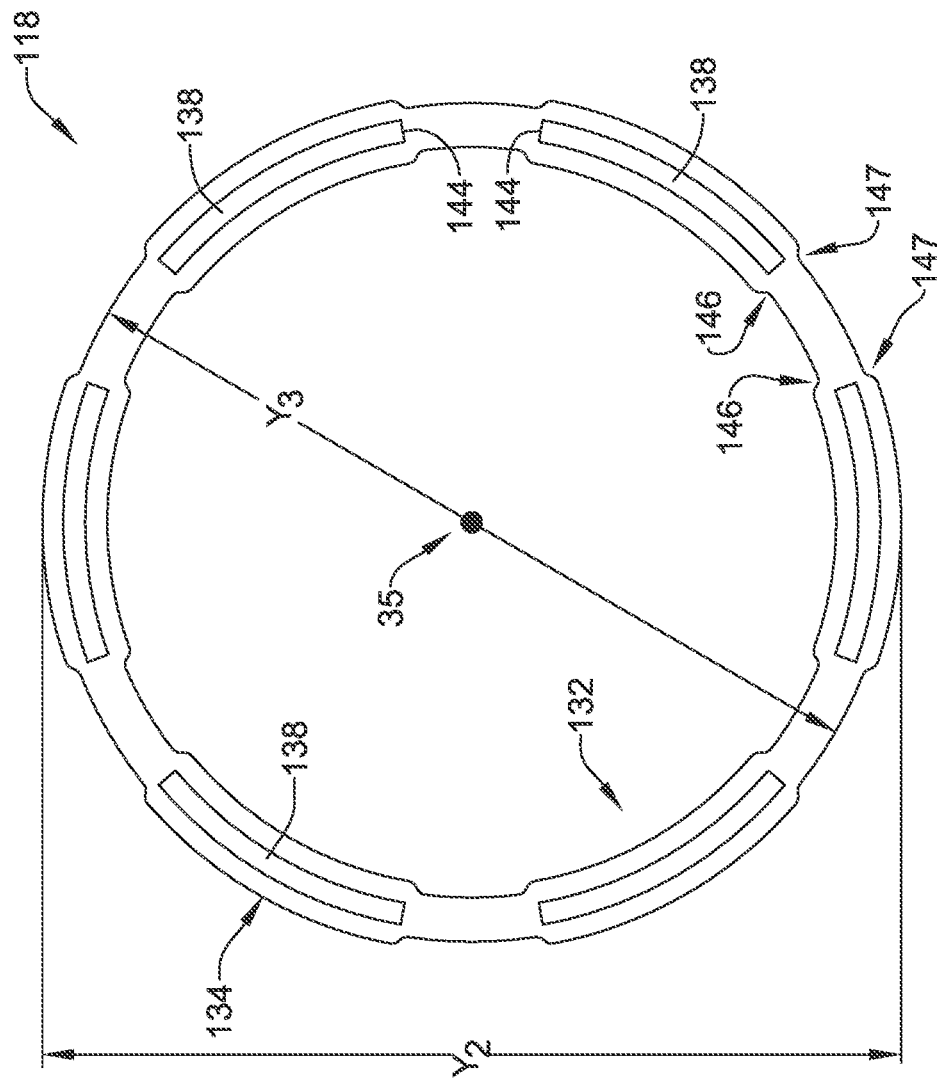
FIG. 4 is a cross-sectional view of an example introducer in an expanded configuration.

FIG. 4 illustrates a cross-section of another example expanded distal section 118 of tubular member 14. Distal section 118 may be similar in form and function to other examples disclosed herein. For example, distal section 118 may include an outer diameter $Y_2$ which may match the expanded outer diameter depicted in FIG. 3. However, FIG. 4 further illustrates that distal section 118 may include a second outer diameter depicted as "$Y_3$." It can be appreciated that the second outer diameter $Y_3$ may be less than the outer diameter $Y_2$. Similar to that described with respect to the wall thicknesses $W_3$ and $W_2$ of FIG. 3, the outer surface 134 of the distal section 118 may taper down radially inward around the ends 144 of the reinforcement members 138. FIG. 4 illustrates that the wall thickness of the distal section 118 of the tubular member 14 may include tapered sections 146 located on the inner surface 132 of the distal section 118 and also may include tapered sections 147 located on the outer surface 134 of the distal section 118. The tapered sections 147 may be defined as a transition region from outer diameter $Y_2$ to outer diameter $Y_3$.

Figure 5:
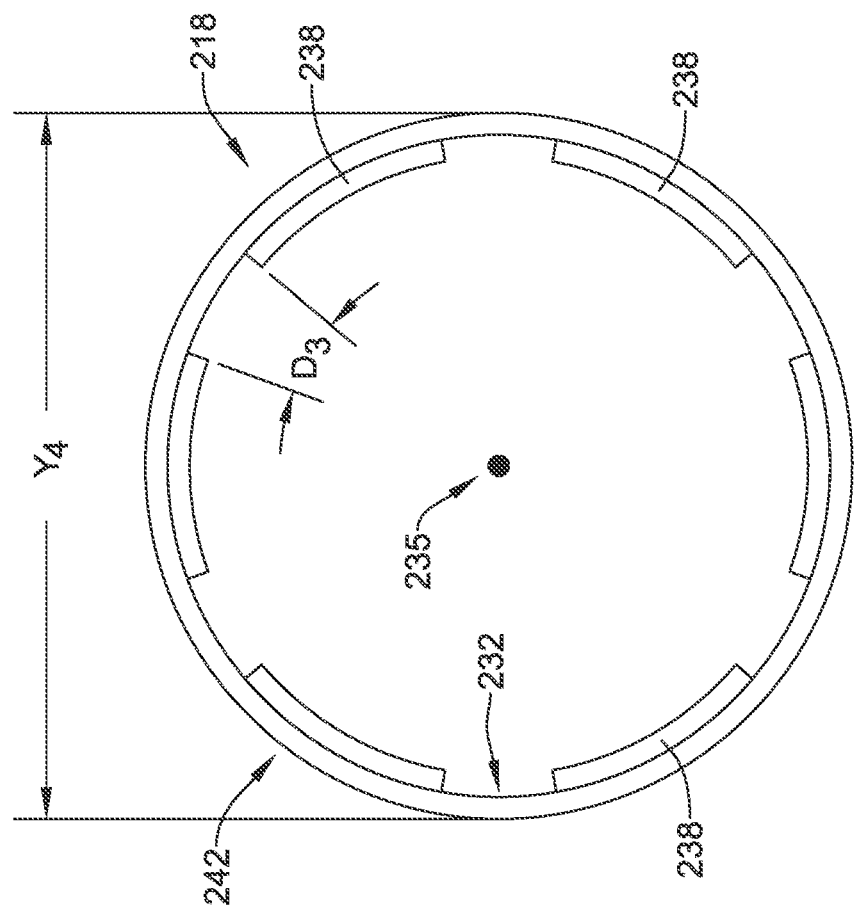
FIG. 5 is a cross-sectional view of another example introducer in an unexpanded configuration.

FIG. 5 illustrates another example distal section 218 of tubular member 14 in a first or unexpanded configuration. Distal section 218 may be similar in form and function to other distal sections described herein. However, distal section 218 illustrates than in some examples, one or more of the reinforcement members 238 may be positioned along the inner surface 232 of distal section 218. For example, the outer surface 242 of one or more of the reinforcement members 238 may be attached to the inner surface 232 of distal section 218. Similar to other examples described herein, the reinforcement members 238 may be circumferentially spaced from one another around the inner surface 232 of distal section 218. In some examples, each of the reinforcement members 238 may be spaced substantially equidistant from one another around the inner surface 232 of distal section 218. However, it is further contemplated that reinforcement members 238 may be spaced at variable distances around longitudinal axis 235.

Similar to the examples illustrated in FIG. 2 and FIG. 3, the distal section 218 of the tubular member 14 shown in FIG. 5 may include an outer diameter depicted as "$Y_4$." Further, FIG. 5 illustrates that each of the reinforcement members 238 may be circumferentially spaced apart from one another around the longitudinal axis 235 of the distal section 218 of the tubular member 14. For example, FIG. 5 shows the reinforcement members 238 may be spaced apart from one another a distance depicted as "$D_3$" in FIG. 5. In some instances, the reinforcement members 238 may be spaced substantially equidistant from one another. In other words, the spacing "$D_3$" may be substantially equivalent between individual reinforcement members 238. However, it is further contemplated that reinforcement members 238 may be spaced at variable distances around longitudinal axis 235. Additionally, it can be appreciated that the distance "$D_3$" depicted in FIG. 5 may vary along the wall thickness of distal section 218.

Figure 6:
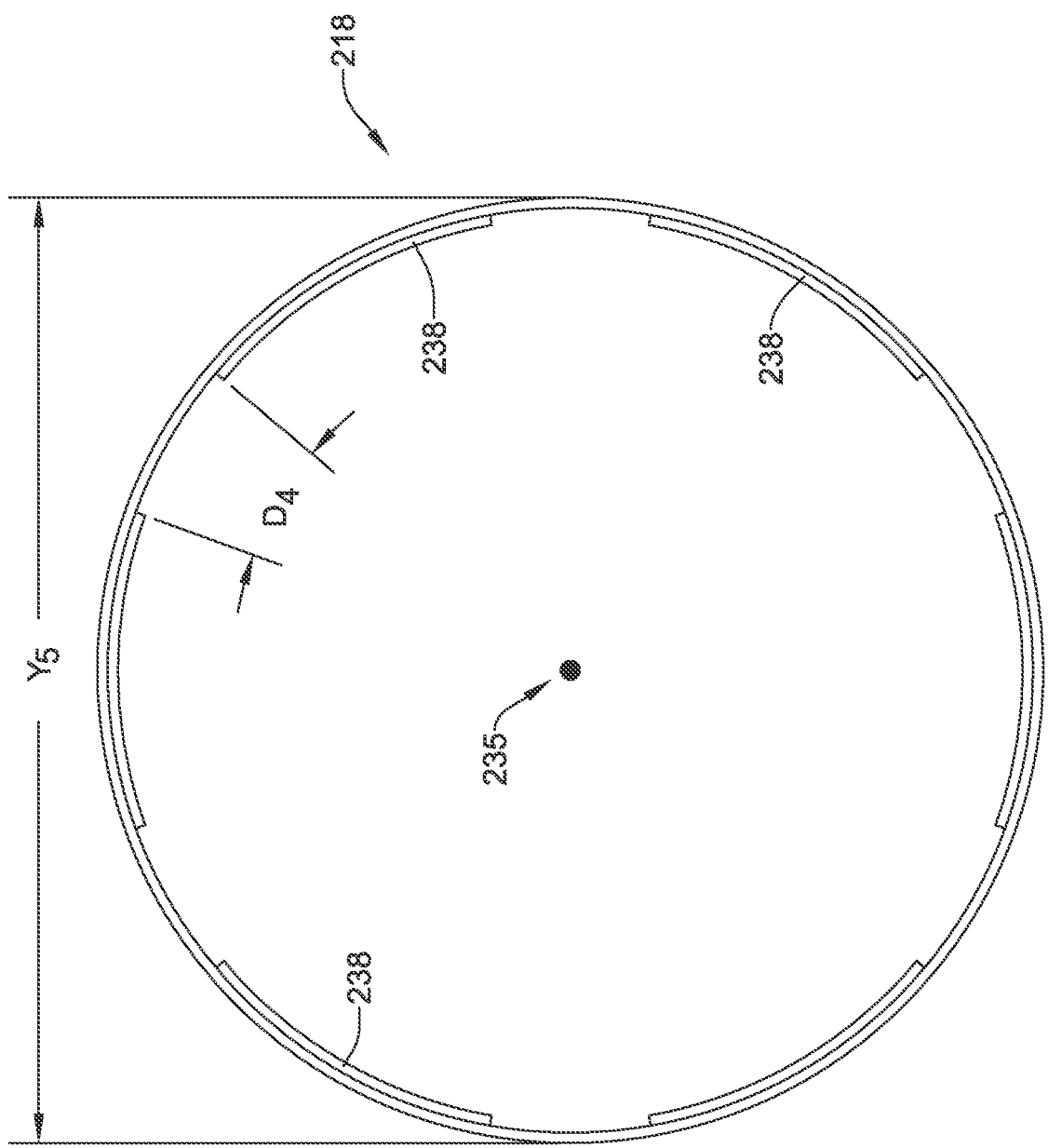
FIG. 6 is a cross-sectional view of the example introducer in FIG. 5 in an expanded configuration.

FIG. 6 represents the distal section 218 of tubular member 14 in a second or expanded configuration. In other words, FIG. 6 may represent the cross-section of the distal section 218 shown in FIG. 5 after it has been expanded radially outward.

As shown in FIG. 6, the distal section 218 of the tubular member 14 may include an outer diameter depicted as "$Y_5$."

It can be appreciated that the expanded outer diameter $Y_5$ may be greater than the unexpanded diameter $Y_4$ shown in FIG. 5.

It can be appreciated that as an example introducer 10 is expanded from an unexpanded configuration to an expanded configuration (as shown in FIG. 5 and FIG. 6, respectively), the wall thickness of the distal section 218 and/or the thickness of the reinforcement members 238 may decrease. In other words, as the distal section 218 of tubular member 14 expands, the material defining the distal section 218 and/or one or more of the reinforcement members 238 may stretch as the distal section 218 of the tubular member 14 expands radially outward. This stretching of the distal section 218 of the tubular member 14 may cause the wall thickness of the distal section 218 to decrease. Further, FIG. 6 shows the space between each of the reinforcement members 238 as "$D_4$." It can be appreciated that as the distal section 218 of tubular member 14 expands, the space between adjacent reinforcement members 238 may increase. In other words, the space $D_4$ may be greater than $D_3$ (depicted in FIG. 5).

Figure 7:
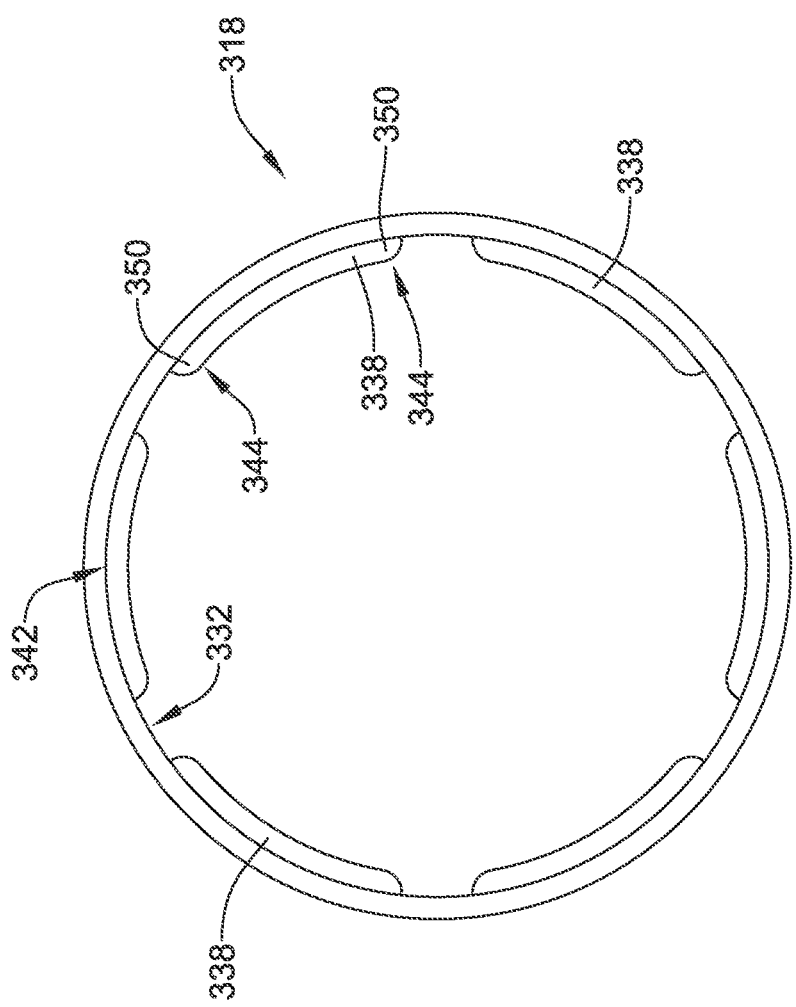
FIG. 7 is a cross-sectional view of another example introducer in an unexpanded configuration.

FIG. 7 illustrates another example distal section 318 of tubular member 14. Distal section 318 may be similar in form and function to other distal sections described herein. For example, distal section 318 illustrates that in some examples, one or more of the reinforcement members 338 may be positioned along the inner surface 332 of distal section 318. For example, the outer surface 342 of one or more of the reinforcement members 338 may be attached to the inner surface 332 of distal section 318. Similar to other examples described herein, the reinforcement members 338 may be circumferentially spaced from one another around the inner surface 332 of distal section 318. In some examples, each of the reinforcement members 338 may be spaced substantially equidistant from one another around the inner surface 332 of distal section 318.

Further, distal section 318 illustrates that one or more of reinforcement members 338 may include end portions 344 having a curved shape 350. For example, FIG. 7 shows the end portions 344 having a rounded or curved shape 350. This curved or rounded shape 350 may reduce the surface area that contacts a medical device which may be passed through distal section 318.

Further, it is contemplated that the inner surface and/or outer surface of tubular member 14 (including proximal section 16, distal section 18 and variations of the distal section 18 described herein) may include one or more layers or coatings, such as a lubricious coating, a hydrophilic coating, a hydrophobic coating, or other suitable coatings, and the like, or may include a lubricant disposed thereon.

Additionally, it is contemplated that in some examples contemplated herein, a liner may be disposed along the inner surface of tubular member 14. It is further contemplated that the liner may extend along the length of tubular member 14, for example, the liner may extend along the distal section 14, the proximal section 16 or both the distal section 14 and the proximal section 16.

In some examples, the example expandable introducer 10 may be disposed about or inserted over a guidewire (not shown), although the guidewire is not required. As discussed above, in some examples the expandable introducer 10 may include a proximal section 16 and a distal section 18. In examples having a proximal section 16, the proximal section 16 may have an inner diameter or extent sufficient to accept a medical device passing therethrough, while the distal expandable section 18 may have an inner diameter or radial extent in a relaxed condition that is less than a maximum outer diameter or extent of the medical device. The expandable introducer 10 may be formed using any of the techniques or structures discussed herein.

Figure 8:
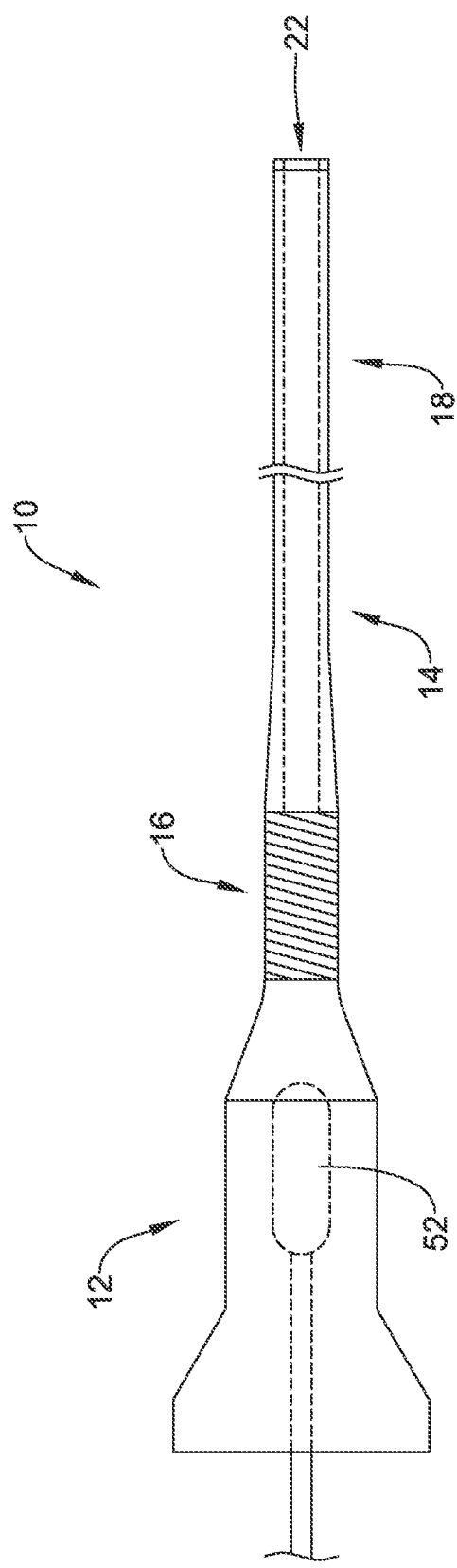
FIGS. 8-10 illustrate an example medical device being inserted through an example introducer.
Figure 9:
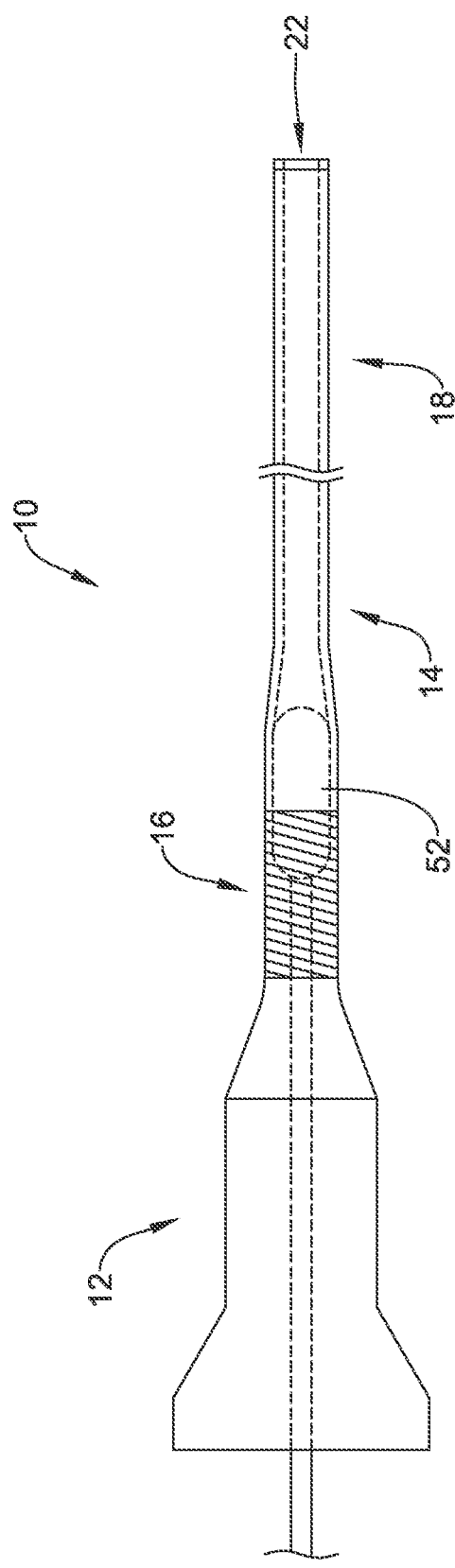
Figure 10:
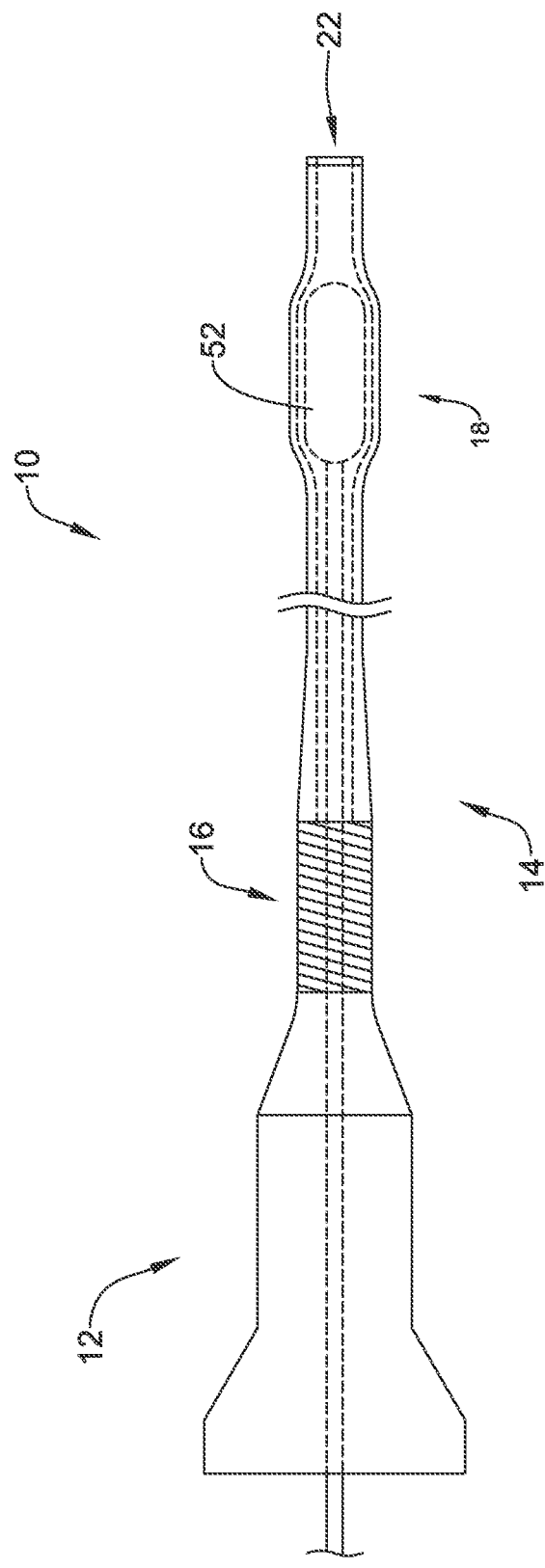

FIGS. 8-10 illustrate a method of use of introducer 10. FIG. 8 shows that an elongate medical device 52 (e.g., heart valve) may be inserted into the lumen 22 of the introducer 10 and advanced distally toward the distal end of introducer 10. As the medical device reaches, encounters, and/or engages the lumen 22 of the introducer 10, the medical device may exert a radially outward force from within the lumen 22 upon the wall of the tubular member 14. The radially outward force may cause the tubular member 14 to expand as the medical device 52 is advanced distally through the proximal section 16 and/or the distal section 18.

FIG. 9 illustrates the medical device 52 being inserted through proximal section 16 and into the distal section 18. As can be appreciated from FIG. 9 and the above discussion, the distal section 18 may expand radially outward as the medical device 52 is inserted therethrough.

FIG. 10 illustrates the medical device 52 being positioned within the distal section 18 of introducer 10. As can be appreciated from FIG. 10, the distal section 18 may expand radially outward in order to permit medical device 52 to travel therethrough. Further, FIG. 10 illustrates distal section 18 contracting (e.g., returning) to an unexpanded diameter as the medical device 52 travels therethrough. In other words, in some examples, the distal section 18 of introducer 10 may be designed such that it can expand radially outward and then contract radially inward as medical devices are inserted therethrough. The expansion of the distal section 18 from an unexpanded configuration to an expanded configuration illustrated in FIG. 10 may correspond to the expansion from an unexpanded to an expanded configuration of the tubular members illustrated and described above with respect to FIG. 2-7.

Further, the expansion of the distal section 18 of the medical device shown in FIG. 10 from an unexpanded configuration to an expanded configuration may be variable. For example, the diameter of the unexpanded distal section 18 of the medical device 10 may increase to an expanded diameter, after which, it may contract to a diameter that is greater than the diameter of the unexpanded configuration. However, this is not intended to be limiting. It is contemplated that once the unexpanded distal section 18 is expanded, it may remain expanded or it may return to any diameter less than the expanded diameter (including a diameter that is less than the unexpanded diameter).

In some examples, introducer 10 may be made from materials such as metals, metal alloys, polymers, ceramics, metal-polymer composites, or other suitable materials, and the like. Some examples of suitable materials may include metallic materials such as stainless steels (e.g. 304v stainless steel or 316L stainless steel), nickel-titanium alloys (e.g., nitinol, such as super elastic or linear elastic nitinol), nickel-chromium alloys, nickel-chromium-iron alloys, cobalt alloys, nickel, titanium, platinum, or alternatively, a polymeric material, such as a high performance polymer, or other suitable materials, and the like. The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL).

In some examples, the introducer 10 may be made from materials such as, for example, a polymeric material, a ceramic, a metal, a metal alloy, a metal-polymer composite, or the like. Examples of suitable polymers may include polyurethane, a polyether-ester such as ARNITEL® available from DSM Engineering Plastics, a polyester such as HYTREL® available from DuPont, a linear low density polyethylene such as REXELL®, a polyamide such as DURETHAN® available from Bayer or CRISTAMID® available from Elf Atochem, an elastomeric polyamide, a block polyamide/ether, a polyether block amide such as PEBA available under the trade name PEBAX®, silicones, polyethylene, Marlex high-density polyethylene, polyetheretherketone (PEEK), polyimide (PI), and polyetherimide (PEI), a liquid crystal polymer (LCP) alone or blended with other materials. In some examples, a suitable polymeric material may have a yield strain of at least 20%, at least 30%, at least 40%, at least 50%, or more. In some examples, the sheath, the membrane, and/or the plurality of corrugations may be made from a material having a low coefficient of friction. In some examples, the sheath, the membrane, and/or the plurality of corrugations may be formed from a fluoropolymer, such as polytetrafluoroethylene (PTFE) or fluorinated ethylene propylene (FEP).

Portions of introducer 10 may be made of, may be doped with, may include a layer of, or otherwise may include a radiopaque material. Radiopaque materials are understood to be materials capable of producing a relatively bright image on a fluoroscopy screen or another imaging technique such as X-ray during a medical procedure. This relatively bright image aids the user of device in determining its location. For example, one or more of the elements described above (i.e., the sheath, the membrane, the medical device, etc.) may include or be formed from a radiopaque material. Suitable materials can include, but are not limited to, bismuth subcarbonate, iodine, gold, platinum, palladium, tantalum, tungsten or tungsten alloy, and the like.

It should be understood that although the above discussion was focused on percutaneous medical procedures within the vasculature of a patient, other examples or methods in accordance with the disclosure can be adapted and configured for use in other parts of the anatomy of a patient. For example, devices and methods in accordance with the disclosure can be adapted for use in the digestive or gastrointestinal tract, such as in the mouth, throat, small and large intestine, colon, rectum, and the like. For another example, devices and methods can be adapted and configured for use within the respiratory tract, such as in the mouth, nose, throat, bronchial passages, nasal passages, lungs, and the like. Similarly, the devices and methods described herein with respect to percutaneous deployment may be used in other types of surgical procedures as appropriate. For example, in some examples, the devices may be deployed in a non-percutaneous procedure. Devices and methods in accordance with the disclosure can also be adapted and configured for other uses within the anatomy.

It should be understood that this disclosure is, in many respects, only illustrative. Changes may be made in details, particularly in matters of shape, size, and arrangement of steps without exceeding the scope of the disclosure. The disclosure's scope is, of course, defined in the language in which the appended claims are expressed.

What is claimed is:

1. An introducer sheath, comprising:
a tubular member including a longitudinal axis, an inner surface, an outer surface defining a circular outer profile, and a wall extending therebetween; and
a plurality of spine members;
wherein each of the plurality of spine members are positioned radially inward of the outer surface of the tubular member;
wherein each of the plurality of spine members are positioned radially outward of the inner surface of the tubular member;
wherein the tubular member is designed to shift from a first configuration to a second configuration;
wherein the wall has a first thickness in the first configuration and a second thickness in the second configuration,
wherein the second thickness is smaller than the first thickness,
wherein the wall has a third thickness in the second configuration,
wherein the third thickness is located between adjacent spine members,
wherein each of the plurality of spine members is positioned within the second thickness of the wall in the second configuration, and,
wherein the third thickness is smaller than the second thickness.

2. The introducer sheath of claim 1, wherein each of the plurality of spine members are embedded within the wall of the tubular member.

3. The introducer sheath of claim 1, wherein each of the plurality of spine members are circumferentially spaced away from one another around the longitudinal axis of the tubular member.

4. The introducer sheath of claim 1, wherein the tubular member includes a proximal region and a distal region, and wherein each of the plurality of spine members extends from the proximal region to the distal region.

5. The introducer sheath of claim 4, wherein each of the plurality of spine members extends helically around the longitudinal axis of the tubular member.

6. The introducer sheath of claim 1, wherein the wall tapers from the third thickness to the second thickness.

7. The introducer sheath of claim 1, wherein the tubular member includes a first outer diameter in the first configuration and a second outer diameter in the second configuration, and wherein the second outer diameter is larger than the first outer diameter.

8. The introducer sheath of claim 7, wherein the tubular member includes a third outer diameter in the second configuration and wherein the third outer diameter is smaller than the second outer diameter.

9. The introducer sheath of claim 8, wherein the tubular member includes a first inner radius in the first configuration and a second inner radius in the second configuration, the second inner radius larger than the first inner radius.

10. The introducer sheath of claim 9, wherein the tubular member includes a third inner radius in the second configuration, and wherein the third inner radius is larger than the second inner radius.

* * * * *